(12) United States Patent
Irick, Jr. et al.

(10) Patent No.: US 11,759,002 B2
(45) Date of Patent: Sep. 19, 2023

(54) SYSTEM AND METHOD FOR LOW VELOCITY AERIAL SUPPLY DROP

(71) Applicant: Five Forces, SPC, Seattle, WA (US)

(72) Inventors: John Thomas Irick, Jr., Seattle, WA (US); Hung-Chi Wang, Seattle, WA (US); Robert E Breidenthal, Jr., Seattle, WA (US); Toni Marie Carlstrom, Seattle, WA (US)

(73) Assignee: Five Forces, SPC, Seattle, WA (US)

( * ) Notice: Subject to any disclaimer, the term of this patent is extended or adjusted under 35 U.S.C. 154(b) by 129 days.

(21) Appl. No.: 17/163,298

(22) Filed: Jan. 29, 2021

(65) Prior Publication Data

US 2021/0237873 A1  Aug. 5, 2021

Related U.S. Application Data

(60) Provisional application No. 62/968,300, filed on Jan. 31, 2020.

(51) Int. Cl.
| | | |
|---|---|---|
| *B64D 1/08* | (2006.01) | |
| *B64D 19/02* | (2006.01) | |
| *A45F 3/14* | (2006.01) | |
| *A61F 17/00* | (2006.01) | |
| *A45F 3/00* | (2006.01) | |

(52) U.S. Cl.
CPC ............ *A45F 3/14* (2013.01); *B64D 1/08* (2013.01); *B64D 19/02* (2013.01); *A45F 2003/003* (2013.01); *A45F 2003/144* (2013.01); *A45F 2200/0583* (2013.01); *A61F 17/00* (2013.01)

(58) Field of Classification Search
CPC ................................. B64D 1/08; B64D 19/02
See application file for complete search history.

(56) References Cited

U.S. PATENT DOCUMENTS

| | | | |
|---|---|---|---|
| 1,901,957 | A | 3/1933 | Girdwood |
| 3,119,196 | A | 1/1964 | Dominec et al. |
| 3,353,295 | A | 11/1967 | Downey |
| 3,665,641 | A | 5/1972 | Henderson |
| 3,860,203 | A | 1/1975 | Hyde |

(Continued)

FOREIGN PATENT DOCUMENTS

| | | | |
|---|---|---|---|
| CA | 2363142 A1 | 5/2003 | |
| CA | 2377291 C | 5/2008 | |

(Continued)

OTHER PUBLICATIONS

Ralph D Lorenz, Spinning Flight Dynamics of Frisbees, Boomerangs, Samaras and Skipping Stones.

(Continued)

*Primary Examiner* — Brady W Frazier
*Assistant Examiner* — Shanna Danielle Glover
(74) *Attorney, Agent, or Firm* — TBillick Law PLLC (57) ABSTRACT

A supply drop assembly for delivering one or more payloads via an aerial vehicle, the assembly comprising a payload body configured to receive a payload; and one or more wings attached to the payload with a connector or integral to the one or more wings; wherein when the supply drop assembly is dropped from the aerial vehicle, the one or more wings start rotating thereby generating lift and slowing the rate of descent of the payload as it falls downwards to a recipient.

9 Claims, 9 Drawing Sheets

(56) References Cited

U.S. PATENT DOCUMENTS

| | | | |
|---|---|---|---|
| 4,886,222 | A | 12/1989 | Burke |
| 5,173,069 | A | 12/1992 | Litos et al. |
| 5,947,419 | A | 9/1999 | Warren et al. |
| 6,712,317 | B1 | 3/2004 | Warren et al. |
| 8,104,718 | B2 * | 1/2012 | Shaw .................. B64C 3/30 244/146 |
| 8,899,513 | B1 | 12/2014 | Jameson et al. |
| 9,199,718 | B2 | 12/2015 | Fogarty |
| 11,250,373 | B1 * | 2/2022 | Condron ............ G06Q 10/0875 |
| 2009/0272852 | A1 * | 11/2009 | Reynolds .............. B64D 1/08 244/138 A |
| 2010/0324754 | A1 * | 12/2010 | Barrows .............. B64D 19/02 701/3 |

FOREIGN PATENT DOCUMENTS

| | | | |
|---|---|---|---|
| DE | 102009055616 B4 | 4/2011 | |
| JP | 2017128258 A | 2/2019 | |
| NZ | 546684 A | 6/2008 | |
| WO | WO2012024685 A1 | 2/2012 | |
| WO | WO-2013050564 A1 * | 4/2013 | ............... B64D 1/08 |
| WO | WO2013050564 A1 | 4/2013 | |
| WO | WO-2021056080 A1 * | 4/2021 | ........... B64C 11/001 |

OTHER PUBLICATIONS

Azuma, Akira; Yasuda, Kunio, Flight Performance of Rotary Seeds, 1989.

Crimi, Peter, Analysis of Samara-Wing Decelerator Steady-State Charachteristics, Jan. 1988.

Green, Douglas S., The Terminal Velocity and Dispersal of Spinning Samaras, American Journal of Botany, Sep. 1980 vol. 67, No. 8 pp. 1218-1224.

Miyahara, Kota, Aerodynamic force acting on the seeds of Ash tree with spin and rotation.

Brunk, James E., Flight Dynamics of Samara-type Single-wing Autorotors, May 2017.

Win, Shane Kyi Hla; Win, Luke Soe Thura; Sufiyan, Danial; Soh, Gim Song; Foong, Shaphui, Dynamics and Control of a Collaborative and Separating Descent of Samara Autorotating Wings, Jul. 2019, IEEE robotics and Automation Letters vol. 4, No. 3.

D. Lentink, W. B. Dickson., J. L. Van Leeuwen, M. H. Dickinson, Leading-Edge Vortices Elevate Lift of Autorotating Plant Seeds, Jun. 12, 2009, Science, New Series, vol. 324, No. 5933, pp. 1438-1440.

Kellas, Andreas, The Guided Samar: Design and Development of a Controllable Single-Bladed Autorotating Vehicle, Sep. 2007.

Li Xue, Linbo Jia, Gi-Soo Nam, Yongjiang Huang, Shitao Zhang, Yuqing Wang, Zhuo Zhou, Yongsheng Chen, Involucre fossils of Carpinus, a northern temperate element, from the Miocene of China and the evolution of its species diversity in East Asia, Mar. 19, 2020.

Shane Kyi Hla Win, Chee How Tan, Danial Sufiyan Bin Shaiful, Jun En Low, Gim Song Soh, Shaohui Foong, The Effects of Chrodwise Wing Optimization of Single-Winged Samara in Autorotation, Jul. 2017.

"Zipline," retrieved Jan. 29, 2021, <https://flyzipline.com>, 9 pages.

"Wingcopter," retrieved Jan. 29, 2021, <https://wingcopter.com>, 7 pages.

"Wing for Aid," retrieved Feb. 1, 2021, <https://www.wingsforaid.org>, 3 pages.

"SkyLIFE Technology," retrieved Jan. 29, 2021, <https://www.skylifeglobal.com>, 4 pages.

"SkyLIFE Global," retrieved Jan. 29, 2021, <https://www.becomeaskylifelicensee.com>, 2 pages.

"ICRA2018—Direction Controlled Descent of Samara Autorotating Wings (SAW)," published Jun. 5, 2019, <https://www.youtube.com/watch?v=fv57Ffrih2o&ab_channel=AIRLab>, 1 page.

Aviation Oil Outlet, "The Mesmerizing Flight Patterns of Maple Seeds Have Inspired a Drone Prototype," published Sep. 6, 2016, <https://aviationoiloutlet.com/blog/maple-seeds>, 6 pages.

Twitter post by Ross Dynamic Lab, published Aug. 2, 2017, <https://twitter.com/RossDynamicsLab/status/892857907502501888>, 1 page.

Turner, Mark G., Decelerator Inspired by Maple Seed, 1 page.

"CopterBox: A Lightweight, Disposable Air Cargo Delivery System", retrieved Mar. 9, 2021, <http://www.dropmaster.com/>, 4 pages.

* cited by examiner

SYSTEM AND METHOD FOR LOW VELOCITY AERIAL SUPPLY DROP

PRIORITY CLAIM

This application claims the benefit of U.S. provisional application No. 62/968,300, filed Jan. 31, 2020, the contents of which are incorporated by reference.

FIELD OF THE INVENTION

The present invention relates to package delivery systems, and more particularly relates to a system and method for a low velocity aerial supply drop.

BACKGROUND OF THE INVENTION

Air delivery systems allow a faster response time than delivery by ground or sea. The faster response time is due to a speed of an aerial vehicle delivering a package and the ability of the aerial vehicle to navigate to a drop location with a more efficient route than vehicles on land. When an active or recent natural disaster has created dangerous or unpassable conditions on the ground, and people are in urgent need of supplies, delivering supplies by air is generally regarded as the fastest way to provide relief to an affected area. The air delivery of supplies is also used in remote areas where land vehicles are not adapted to traverse terrains, or when supplies are needed quickly such as for a medical emergency. Some commercial deliveries are also made by air.

Air delivery systems can be simplified into three primary aspects: an aerial vehicle, a payload, and a delivery mechanism. The aerial vehicle transports one or more payloads to the drop site. The delivery mechanism is a mechanical mechanism or a physical feature of the air package delivery system which allows the payload to descend slowly to the ground.

Some delivery mechanisms are a part of the aerial vehicle and can be configured to be reusable. Parachutes are an example of a delivery mechanism that is attached to, and descends with, the payload. However, parachutes have a variety of failure modes which can result in the package entering "deadfall" (i.e. a descent that is too fast). Parachutes must be carefully folded and packed to ensure proper deployment, and they must also be inspected before use to ensure mechanical integrity and that they are properly attached to the payload. Due to these and other limitations, parachutes take time, skill, and care to pack. In a disaster scenario, time is critical in which air delivery systems are typically used. In a non-disaster scenario, time and resources should also be prioritized. There is a need in the art for a package and delivery mechanism that is quicker and easier to prepare and deploy.

Additionally, parachutes are typically made of materials such as plastic or fabric which do not readily decompose in the environment. During mass deployment of disaster supplies, some parachutes will accordingly cause adverse effects to the environment. There is a need in the art for a mass deployable air delivery system that is environmentally friendly, specifically by being easily decomposable, so as not to adversely affect the environment.

The material used for the package and the descent mechanism, if it falls with the package, should optionally withstand use in a wet environment so that people can find the package and remove the useful supplies. Yet, many disaster situations such as floods, typhoons, or tsunamis involve wet conditions, decreasing the probability of usability of package delivery systems using rapidly disintegrating materials. There is a need in the art for a delivery system that does not become unusable due to wet conditions.

The cost of a parachute relative to the cost of the payload is also disproportionately large, especially in disaster relief situations where the supplies being delivered are relatively inexpensive staples such as clean water or food. There is a need in the art for a less expensive solution.

To address the aforementioned issues with a parachute delivery assembly, there is a need in the art to develop a system and method for a low velocity aerial supply drop that does not principally rely upon a parachute.

SUMMARY OF THE INVENTION

In view of the foregoing, embodiments herein provide a supply drop assembly for delivering one or more payloads via an aerial vehicle. The assembly includes a payload body and one or more wings. The payload body is configured to receive a payload and may optionally be fully integrated with at least one or more wings. The one or more wings may also be removably attached to the payload with a connector. When the supply drop assembly is dropped from the aerial vehicle, the one or more wings starts rotating thereby delivering the payload downwards in a rotational manner to a recipient.

Another aspect is a method for deploying supplies via an aerial vehicle. The method includes configuring a payload body to receive a payload thereupon. The method further includes attaching one or more wings to the payload body with one or more connectors, such that the payload body and the attached one or more wings will tend when in contact with the atmosphere in freefall, to autorotate. In turn, this slows a rate of descent of the payload body to prevent damage to the payload.

These and other aspects of the embodiments herein will be better appreciated and understood when considered in conjunction with the following description and the accompanying drawings. It should be understood, however, that the following descriptions, while indicating selected embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

Preferred and alternative examples of the present invention are described in detail below with reference to the following drawings.

DETAILED DESCRIPTION OF THE DRAWINGS

While the preferred embodiment of the invention has been illustrated and described, as noted above, many changes can be made without departing from the spirit and scope of the invention. Accordingly, the scope of the invention is not limited by the disclosure of the embodiments below. Instead, the invention should be determined entirely by reference to the claims that follow.

As mentioned, there remains a need for a supply drop assembly. The embodiments herein achieve this by providing the supply drop assembly with one or more wings. The supply drop assembly can be built according to a samara seed found in nature, and the assembly can emulate a samara seed found in nature as it descends from a plant or tree. Referring now to the drawings, and more particularly to FIGS. 1 through 9C, where similar reference characters denote corresponding features consistently throughout the figures, there are shown preferred embodiments.

Figure 1:
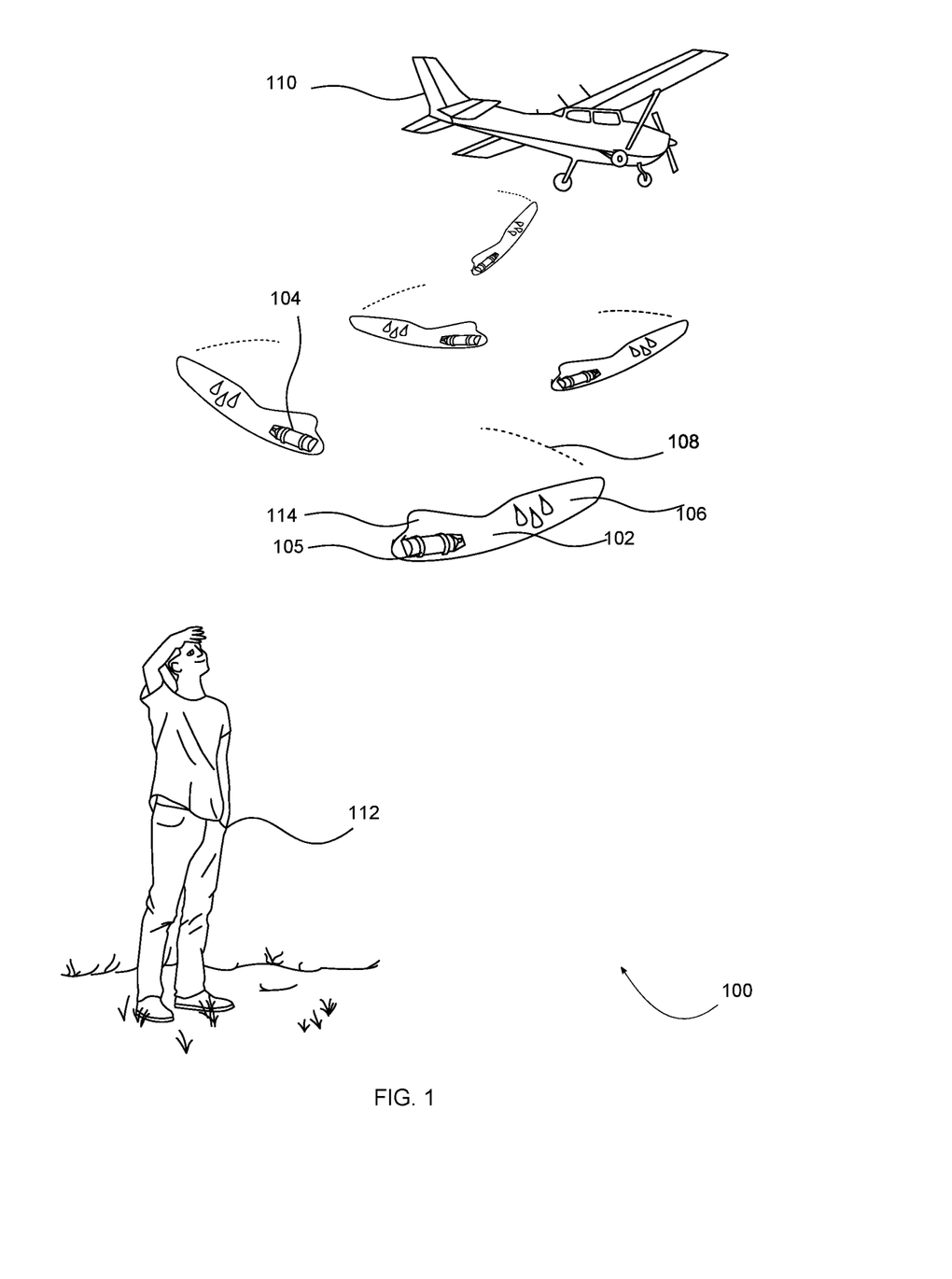
FIG. 1 shows an example of a supply drop procedure, where a recipient on the ground is looking up at a number of supply drop assemblies carrying supplies that have been dropped from an aerial vehicle.

FIG. 1 shows an example of a supply drop procedure, where a recipient 112 on the ground is looking up at a number of supply drop assemblies carrying supplies that have been dropped from an aerial vehicle 110, according to various embodiments herein. The supply drop procedure is carried out by the system for a low velocity aerial supply drop. The system includes a supply drop assembly 100 for deploying the supplies via the aerial vehicle 110. The supply drop assembly 100 includes a payload body 102, the payload body 102 having a payload 104, one or more wings 106, optionally a connector 105, and optionally a lobe 114. The assembly 100 when dropped from the sky via the aerial vehicle 110 rotates or spins as it descends down to the recipient 112 via rotational path 110. The payload 104 may include water, food, tools, survival supplies, and the like. The supply drop assembly 100 is optionally configured to include the lobe 114 near a center of gravity of the assembly 100. The assembly 100 emulates a samara seed found in nature as it descends from a plant or tree. The lobe 114 causes the one or more wings 106 of the assembly 100 to generate additional thrust; and the additional thrust is useful in helping the one or more wings 106 to enter autorotation, by moving a center of aerodynamic forces during free-fall before the autorotation back towards a trailing edge of the one or more wings 106. Hereinafter the supply drop assembly, samara style assembly, and the assembly will be used interchangeably throughout the disclosure.

In some embodiments, the payload 104 may be made up of multiple items, and the multiple items may be enclosed in assembly 100, or in a separate enclosure attached to the one or more wings 106. The payload 104 may be attached directly to the payload body 102 which in turn may be integrated directly into the one or more wings 106, or through a connector, fixably attached, or a flexible material or assembly which is flexible. It may also be attached by a coupling mechanism that allows the one or more wings 106 to spin completely freely or more feely relative to the payload 104. Wing load is regarded as weight/wing area; and lower wing load can lead to lower descent speed. The one or more wings 106 can be a simple plate.

In some embodiments, the one or more wings 106 are configured similar to a samara seed, which is a single winged object that enters into and maintains autorotation as it falls. Autorotation slows the fall of the samara leaf. Many principles that apply to the samara leaf also apply to the supply drop assembly's operation.

In some embodiments, the supply drop assembly 100 is a samara style assembly. When the samara style assembly begins to fall, any asymmetry in shape of the assembly or initial orientation will result in a torque acting on the assembly due to the drag force of the air. The torque will cause rotation to begin. The rotation generally begins randomly, but rigid payload body rotation in free space tends towards a lowest energy spin. The samara style assembly's lowest energy rotation would be around the center of gravity with the axis of rotation normal to the plane of the wing. The samara style assembly tends to rotate within a disk of space like the blade of a fan. As the wing 106 rotates, the samara style assembly generates lift. The generated lift force acts near the wing tip, causing the wing to tip up, so that the payload 104 or center of gravity is lower than the wing tip. The centrifugal force balances the lift force, as the centrifugal force acts to flatten the samara style assembly.

In some embodiments, once rotation i-s starts, the rotation is maintained through a fall period until the assembly reaches the ground. The rotation is maintained due to the thrust generated at the root of the rotating wing. The root may be located at a portion of the assembly approximately ¼ the distance between the center of gravity and the wing tip. The samara style assembly orients itself so that the leading edge, which is closer to the center of gravity of the wing, is tilted down or pitched down into the incoming air. The angle of the wing at the root relative to the incoming air pushes the samara style assembly to rotate around the center of gravity in the direction of the leading edge of the wing. The thrust generated near the wing root keeps the assembly rotating. Drag due to rotation balances this thrust so that the assembly reaches rotational equilibrium.

The aerodynamic lift causes the wing to tip up, or roll, and also creates a vertical force resisting the downward force of gravity. The lift force results in the assembly falling more slowly than if in free fall under the influence of gravity.

In some embodiments, the one or more wings 106 may have a flat airfoil profile, a rounded airfoil profile, a squared airfoil profile, a symmetrical airfoil profile, a non-symmetrical airfoil profile, or other shape of airfoil profile. The one or more wings 106 may optionally include a beacon to alert the recipient 112 to locate the assembly 100 when the assembly 100 is lost accidentally. The beacon could emit light or emit a radio frequency signal to help the recipient 112 to locate the assembly 100. The beacon may also be optionally integrated into the payload 104 in addition to or instead of being integrated into the one or more wings 106. Another form of beacon that may be incorporated into the assembly 100 is a noise generating beacon. The noise generating beacon may emit noise using electronics, mechanical means, or the noise generating beacon may whistle as the beacon moves through the air. All of the optional beacons help the recipient 112 to locate the assembly 100 and alert the recipient 112 to the beacon's presence. Some embodiments also incorporate colorations or symbols for recipients to visually spot and recognize the contents of a falling or fallen assembly. The colorations or symbols may be incorporated into a design or material choice of the one or more wings 106 and the payload 104.

In some embodiments, the one or more wings 106 and the payload 104 may be configured such that the density of the payload 104 is less than the density of water. Materials used to construct the assembly 100 would not degrade rapidly if the assembly 100 falls into water. The material allows the assembly to float on water and allows potential recipients to retrieve the assembly 100 and extract the contents of the payload 104. The center of gravity may be configured so that the one or more wings 106 sticks vertically out of any water the assembly lands in when it is free floating.

Figure 2:
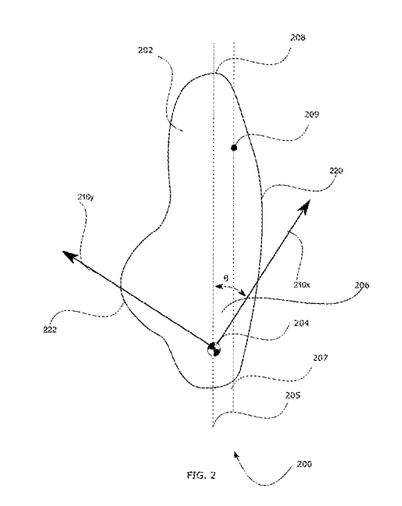
FIG. 2 shows a top view of an example of a supply drop assembly that has one or more fixed wings.

FIG. 2 shows a top view of a first example of a supply drop assembly that has one or more fixed wings. For clarity and not limitation, FIG. 2 shows an assembly with one wing. The assembly 200 has a center of gravity 204 located near a root portion 206 of the assembly 200. From the center of gravity 204, two perpendicular vectors Ipx 210x, and Ipy 210y extend. The perpendicular vector Ipx 210x is a vector representing an axis around which the assembly 200 that has a lowest mass moment of inertia. The perpendicular vector Ipy 210y is a secondary moment of inertia vector. The magnitude of the Ipy vector 210y may be less than or equal to the magnitude of the Ipx vector 210x as a way to encourage the wing 202 to enter automatic rotation. For example, the ratio of the magnitudes Ipx/Ipy may be above 0.492 to encourage the wing 202 to enter automatic rotation.

A spanwise axis 205 extends through the center of gravity 204 along a length of the assembly 100. To the right of the spanwise axis 205, towards the fixed wing's 202 leading edge 220, is an approximately ¼ chord station axis 207. An angle between the Ipx 208 and the spanwise axis 205 is angle θ. As the assembly 200 rotates, the fixed wings 202 rotate around the center of gravity 204. A distal wing tip 208 will trace a substantially helical path in the air as the assembly descends. Lift will be generated by wing 202, slowing the assembly's 200 fall. The center of aerodynamic lift 209 is located near the ¼ chord station axis 207 and towards the distal wing tip 208. For stability to be achieved during flight, the center of aerodynamic lift 209 preferably will be sufficiently far behind the Ipx 208, causing the assembly 200 to pitch downward so that thrust is generated near one or more fixed wings root 206.

Similar to FIG. 1 optional lobe 114, an optional lobe 222 may be added to one or more fixed wings profiles at an edge of the wing 202 near the center of gravity 204. The lobe 222 causes the one or more fixed wing's root 206 to generate additional thrust and the additional thrust is useful in helping the assembly 200 to enter autorotation, by moving the center of aerodynamic force 209 during free-fall back towards the trailing edge 230 of the wing 202 and away from Ipx 208 before entering autorotation.

Figure 3A:
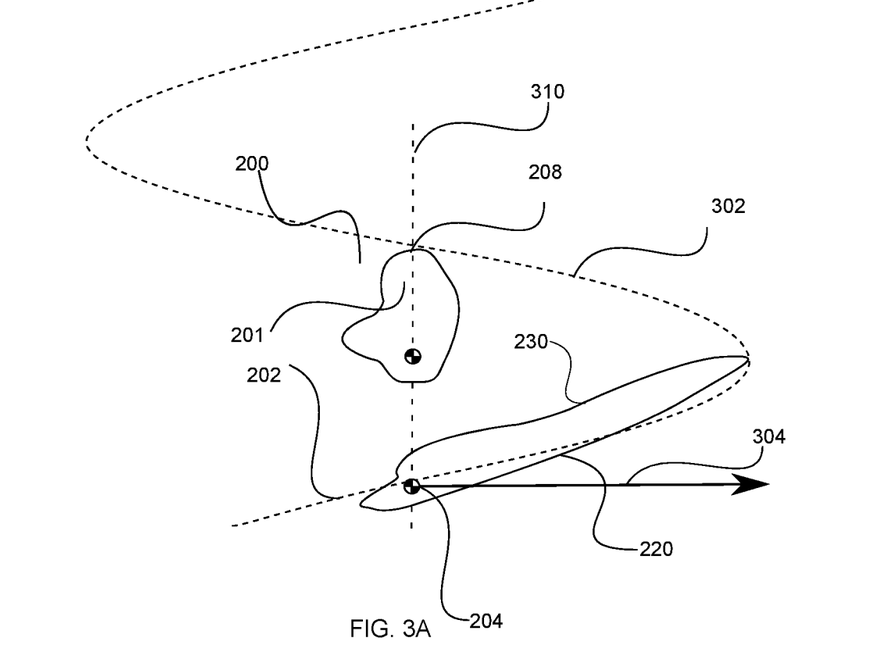
FIG. 3A shows a front view of the supply drop assembly shown in FIG. 2.

FIG. 3A shows a front view of the supply drop assembly shown in FIG. 2. The front view of the assembly 200 shows a clockwise autorotative path that the assembly 200 takes while falling down. The assembly 200 rotates around its center of gravity 204, falling substantially vertically downward through the air. From the front view, the leading edge 220 is seen below a trailing edge 230, as the one or more fixed wing is pitched downward. The perpendicular vector Ipx 304 is pictured as horizontal. The one or more wings pitch downward by rotating about the perpendicular vector Ipx 304, because the perpendicular vector Ipx 304 is the easiest axis for the one or more wings to rotate around. As the one or more wings pitch by rotating around the perpendicular vector Ipx 304, the centrifugal force due to rotation tends to flatten the one or more wings, balancing a pitching force. As a rotation speed increases, the centrifugal force increases. As the centrifugal force increases, the one or more wings pitch less from the downward position, decreasing thrust and therefore decreasing rotational speed. The wing tip 208 traces a helical path 302 around an axis of descent 310, which is vertical in still air, and parallel to the incoming wind from the reference frame of the assembly.

Figure 3B:
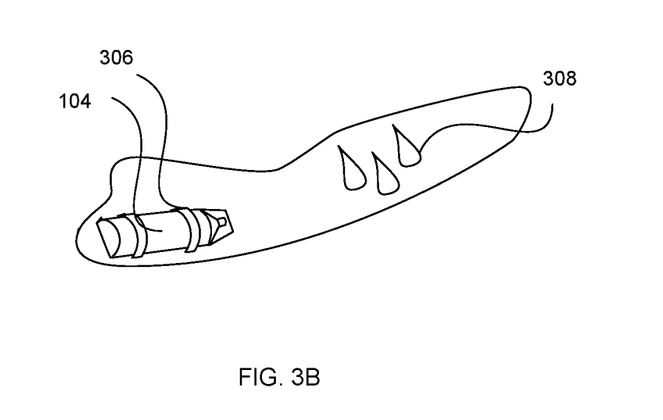
FIG. 3B shows an isometric view of the supply drop assembly of FIG. 2 as configured to carry water as a payload.

FIG. 3B shows an isometric view of the supply drop assembly of FIG. 2 as configured to carry water as a payload, with a water bottle attached with straps 306. The wing is labeled with a graphic of water droplets 308, showing that the payload contains water.

Figure 4:
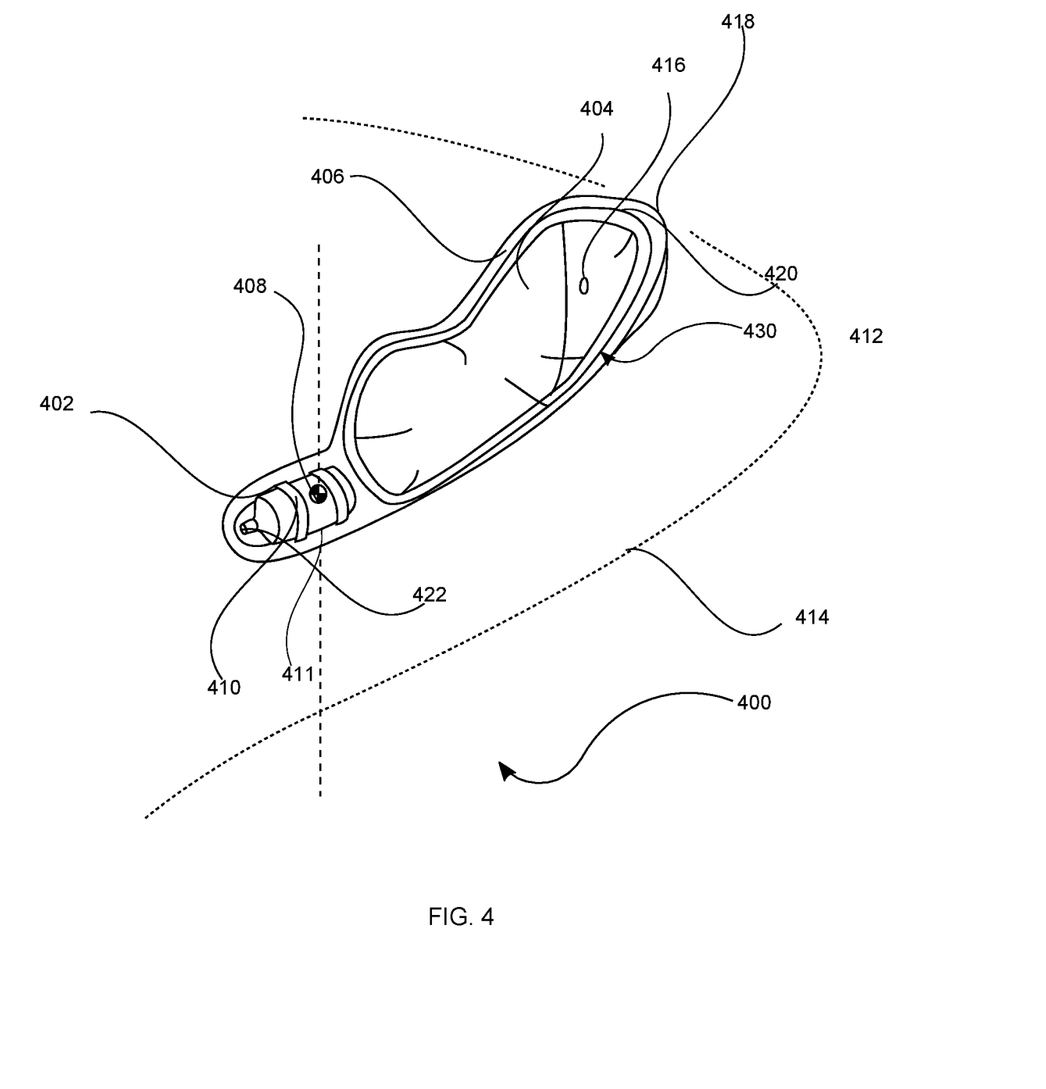
FIG. 4 shows an isometric view of a second example of a supply drop assembly that has one or more inflatable wings.

FIG. 4 shows an isometric view of an example of a supply drop assembly 400 that has one or more inflatable wings 406. The assembly 400 includes an inflatable chamber 404 that can inflate as the assembly falls. An axis of descent of the assembly 400 goes through its center of gravity 408. The payload 402 can be a water bottle, and can be attached rigidly to the wing 406 with one or more straps 410. Other forms of attachment can be used to secure the payload such as rope, buttons, snaps, hook-and-loop fasteners, and the like. There is a cut-out 411 in the assembly where the payload 402 sits, protruding part way to the bottom of the assembly. There is another cutout 420, to which a plastic chamber 404 is attached. The chamber 404 is attached around the rim 430 of the cut-out 420. A first opening 412 is created between two pieces of the wing 406, funneling air near the wing tip 418. The pressure on the wing tip 418 is elevated due to the rotational motion of the wing. The wing tip 418 traces a substantially helical path 414 as it falls. Air passes through the first opening 412, then through a one-way valve 422 and through a second opening 416 into the chamber 404, filling it with air. The air cannot escape as the one-way valve 422 prevents the air from leaving. In some embodiments, the chamber 404 may be filled using a $CO_2$ cartridge, or other forms of compressed air, or other material having a density less than that of water.

Figure 5A:
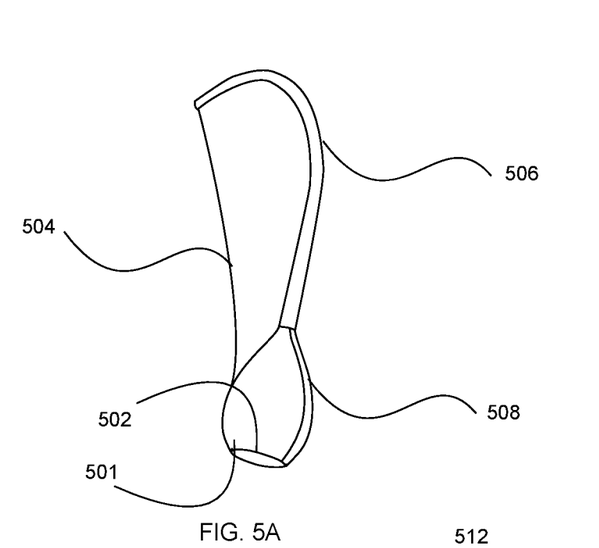
FIG. 5A shows an isometric view of the supply drop assembly of FIG. 4, illustrating the operation of an inflatable chamber within the supply drop assembly that inflates as it falls.
Figure 5B:
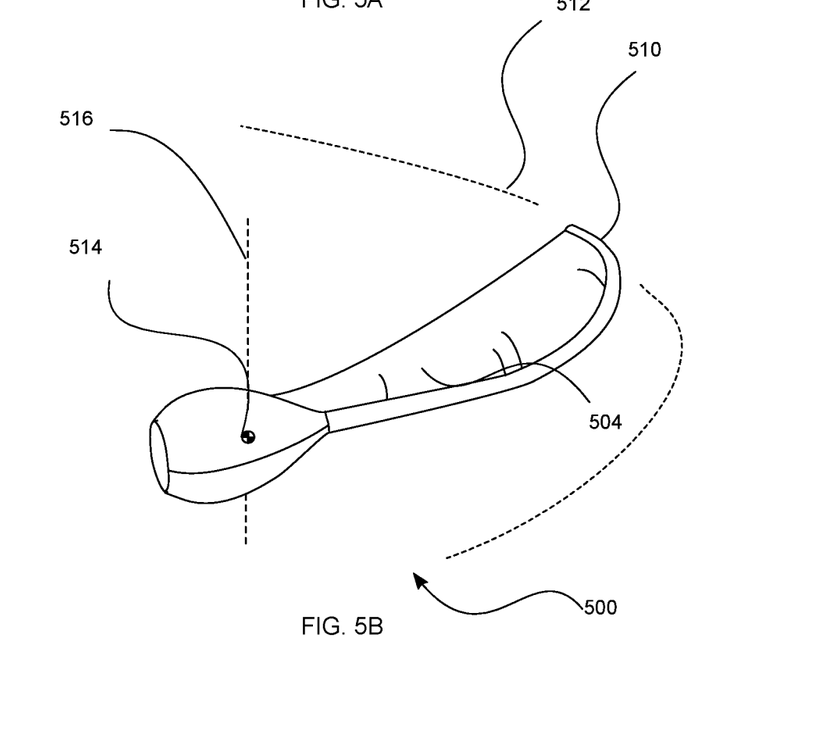
FIG. 5B shows an isometric view of the supply drop assembly of FIG. 5A autorotating clockwise in freefall.

FIGS. 5A and 5B show an isometric view of a supply drop assembly 500, illustrating the operation of an inflatable chamber within the supply drop assembly that inflates as it falls. At the bottom of the assembly, near a base 501, is an opening 502. The inflatable-wing begins rotating by falling straight down, thereby creating an area of elevated pressure near the opening 502. Air passes through the opening 502, and may pass through through a one-way valve to permanently inflate a chamber 504 with air. The air chamber is held in shape with a rib 506. A payload 508 is wrapped near the root 501 of the assembly.

An optional compressed air cartridge decreases an amount of storage space required in the aerial vehicle 110 to store the assembly 100, allowing larger payloads or more payloads to be transported for delivery in the same space. In some embodiments, the structure of the one or more wings is designed in a way that the leading edge is made of a rigid material and a remainder of the one or more wings is configured to inflate as the one or more wings wing is descending.

In some embodiments, the inflatable wings and or payload is intended for use as a flotation device in case of a natural disaster involving flooding or water. In some embodiments, the inflatable wings or payload is large enough when inflated for a person to use it as a raft. In some embodiments, the inflatable wings and or payload is inflated using a compressed gas such as helium which is lighter than air. The payload inflated with the gas allows the assembly to carry a heavier payload to maintain optimal performance. In some embodiments, the inflatable wings and or payload is made of thermally insulative materials and is intended to be used as a sleeping pad or shelter.

FIG. 5B shows an isometric view of the supply drop assembly of FIG. 5A autorotating clockwise in freefall. The supply drop assembly with the inflatable wing autorotates in a clockwise path. The chamber 504 is full of air. A wing tip 510 traces a helical path 512 as the wing rotates around its center of gravity 514 as it falls along its axis of descent 516.

Figure 6A:
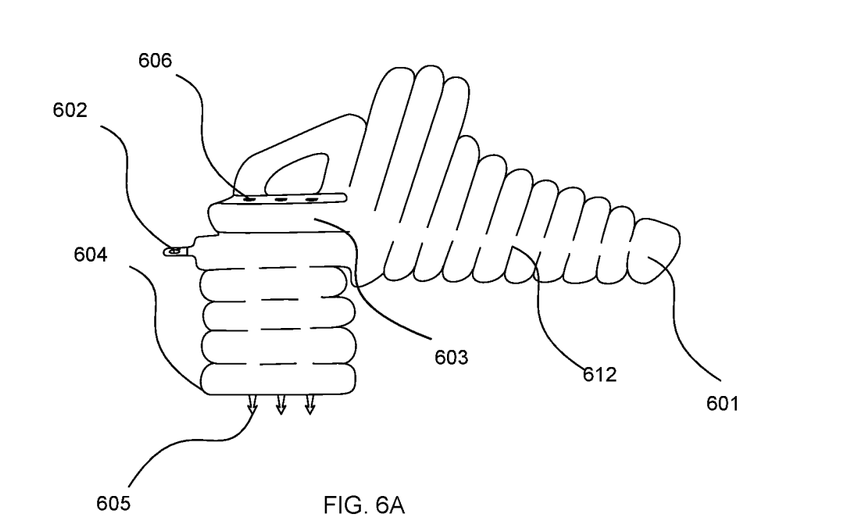
FIG. 6A shows a top view of another example of a supply drop assembly that has one or more pre-inflated wings configured to be inflated prior to delivery.
Figure 6B:
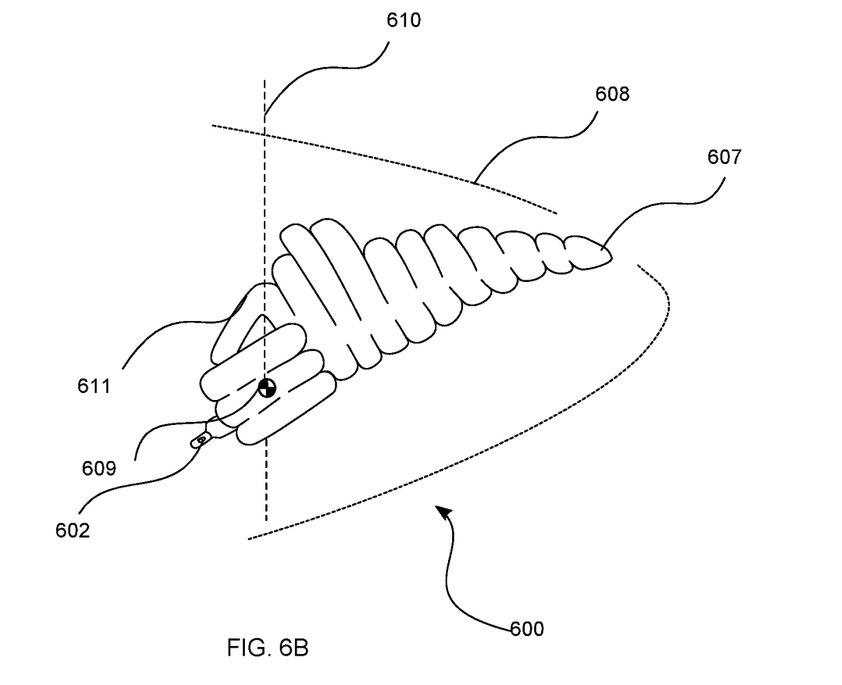
FIG. 6B shows an isometric view of the supply drop assembly of FIG. 6A, with the one or more pre-inflated wings inflated and the supply drop assembly autorotating clockwise during descent.

FIG. 6A shows a top view of another example of a supply drop assembly 600 that has one or more pre-inflated wings 601 configured to be inflated prior to delivery. A fully-inflatable single-wing assembly 600 is constructed using two films of plastic welded together to form an air chamber 612. The wing 601 is inflated through a one-way valve 602. A payload may be secured at location 603, by rolling a set of tubes 604 around the payload, and securing it in place by inserting the barbed tabs 605 through the slots 606. FIG. 6B shows the assembly 600 autorotating as it descends. The wing tip 607 traces a substantially helical path 608 through the air as it rotates around its center of gravity 609 and descends along its axis of descent 610. The chamber 611 is fully inflated, creating a somewhat rigid structure.

The supply drop assembly with the one or more pre-inflated wings includes an air chamber or chambers. The air chamber or chambers are configured with cushion to prevent the payload from being damaged upon impact with the ground. The cushion on the payload may also help to prevent injury to people or animals on the ground. In some embodiments, the payload is attached to the one or more wings. The payload or items may be contained inside the inflatable payload body of the one or more wings. In some embodiments, the inflatable payload body of the one or more wings is wrapped around the payload or items prior to inflation and secured in place by tape, heat sealing, mechanical means, or other means, and the payload or items are secured in place when the payload body is inflated. In other embodiments, the inflated wing structure is wrapped around the payload or items after inflation.

Figure 7A:
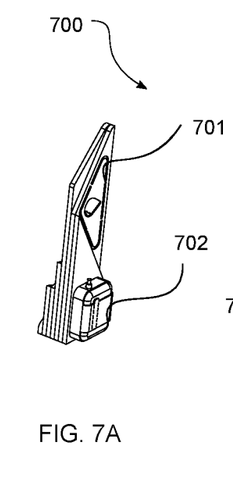
FIG. 7A shows an isometric view of a fourth example of a supply drop assembly that has one or more folding wings.
Figure 7B:
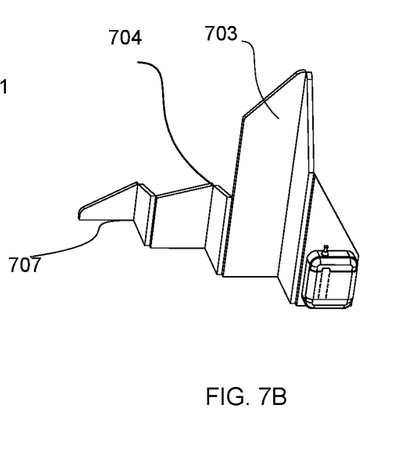
FIG. 7B shows an isometric view of the supply drop assembly of FIG. 7A showing the one or more folding wings in a partially folded configuration.
Figure 7C:
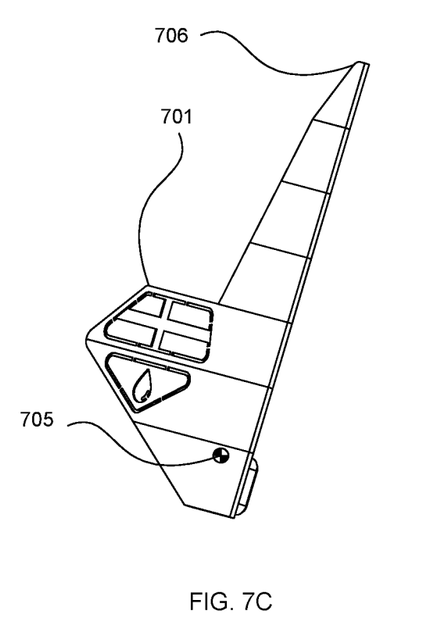
FIG. 7C shows a top isometric view of the supply drop assembly of FIG. 7A and FIG. 7B, showing the one or more folding wings in a fully expanded configuration.
Figure 7D:
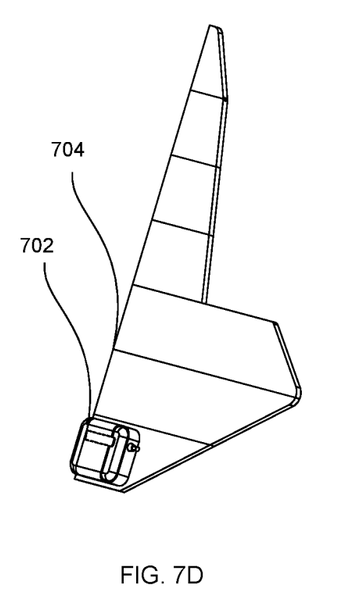
FIG. 7D shows a bottom view of the supply drop assembly of FIG. 7A, FIG. B, and FIG. C, showing the one or more folding wings in a fully expanded configuration.

FIGS. 7A, 7B, 7C, and 7D show an isometric view of a supply drop assembly 700 showing one or more folding wings 707. FIG. 7A shows a folding wing, fully folded to be compact before deployment. The wing may have a graphic 701 indicating the type of payload it contains; and may have a water flask 702 affixed to the wing. FIG. 7B shows the wing of FIG. 7A partially unfolded. The wing 707 is constructed of panels 703 which are attached with thinner material that which act as one or more hinges 704. FIG. 7C shows the wing of FIGS. 7A and 7B fully expanded. The center of gravity 705 of the system is located near the water flask. The wing tip 706 traces a helical path as the assembly autorotates during descent through the air. The assembly may fall with the graphic 701 facing downwards relative to the ground. FIG. 7D shows the same wing, withing hinges 704 and water flask 702 visible.

As shown in FIGS. 7A, 7B, 7C, and 7D, the one or more wings may be made in sections with folds or hinges connecting the sections. One piece of material may be used with folds to create the one or more wings 707. The folds or hinges may be aligned with the airfoil of the wing or may be aligned in another direction. In these embodiments, the assembly is stored in a folded configuration prior to dropping. Upon dropping, at least one wing expands, either under spring pressure or due to the drag caused by the air or by a combination of both. The folded structure creates an asymmetry in the wing which helps create the initial disturbance which leads to the initial rotation. This increases the likelihood that the assembly will enter autorotation. In some embodiments, the assembly is configured asymmetrically with respect to the top and bottom of the wing surface or package geometry in order to create the initial disturbance and increase the likelihood that the samara will enter autorotation. This initial disturbance may be initiated by a flap extending off the tip of the wing, which creates this asymmetry and instability, causing the wing to begin the process of entering autorotation.

Figure 8:
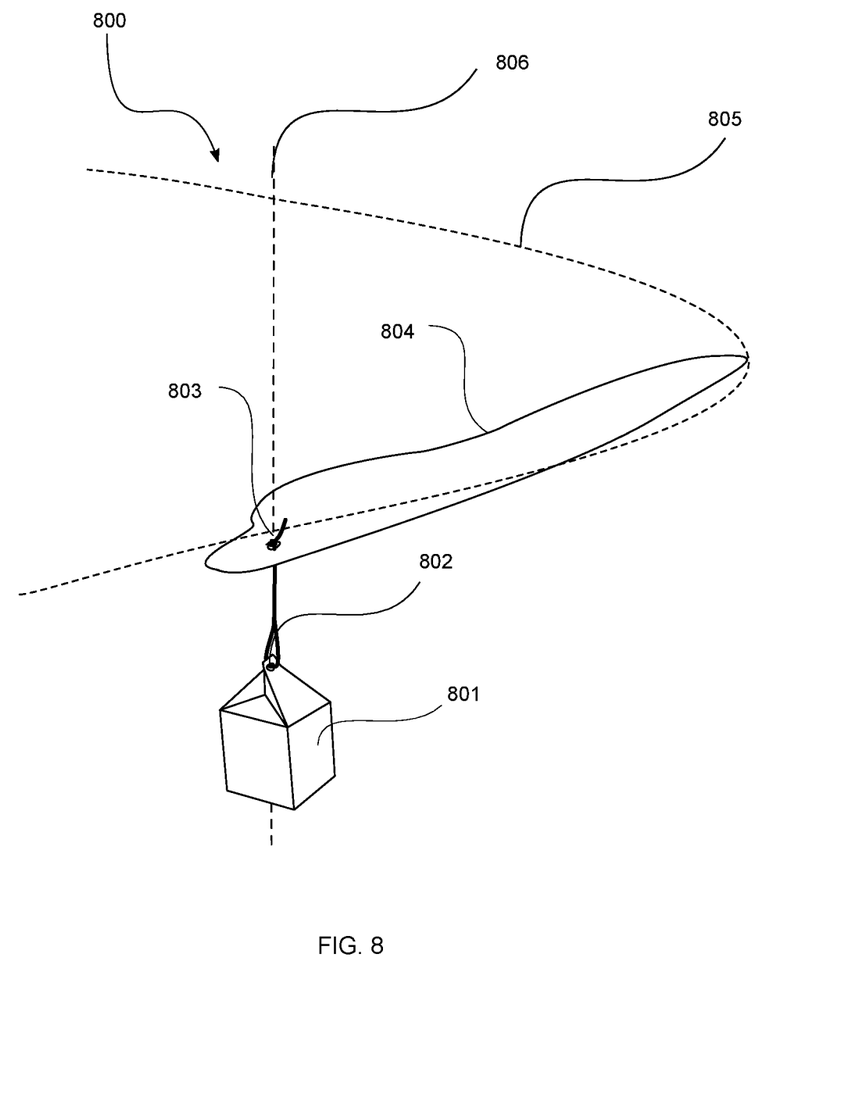
FIG. 8 shows an isometric view of another example of a supply drop assembly with a single wing and an under-slung payload configuration to permit the one or more wings to move independently from a payload.

FIG. 8 shows an isometric view of another example of a supply drop assembly 800 with a single-wing and an underslung payload configuration. The assembly with the single-wing includes a payload 801 attached with a rope 802 strung through a hole 803 in the single-wing 804. The rope 802 is knotted after passing through the hole 803, preventing the payload 801 and the single-wing 804 from coming apart. The single-wing 804 may rotate independent of the payload 801, decoupling the rotational properties of the single-wing 804 from the rotational properties of the payload 801. The single-wing 804 tip traces a helical path 805 as the single-wing 804 falls through the air along the axis of descent 806.

In some embodiments, the one or more wings 106 are attached flexibly to the payload 104 so that the one or more wings 106 may spin freely relative to the payload 104. For the flexible attachment, the payload may be attached to the one or more wings 106 with a string, a rope, a cord, or a rubber strip, or a strap. A swivel joint or a coupling motor or joint may be used in conjunction with or instead of the string, the rope, or the cord to decouple the rotation of the one or more wings 106 from the payload.

In some embodiments, the cord, the swivel, or alternative rotational coupler would be attached at or formed at the desired location of the center of gravity of the assembly. Options for connector include, but are not limited to, inserting a cord through a hole and then tying a knot so it cannot pass through the hole, attaching a string with glue or staples, or using a crimp or sinch. For a rigidly attached string, a longer piece of string will result in weaker coupling.

Optionally, the rotational joint between the wing and the package can be motorized or spring loaded. A motorized or spring-loaded joint can help jump-start the rotation of the wing, ensuring autorotation is entered.

Figure 9A:
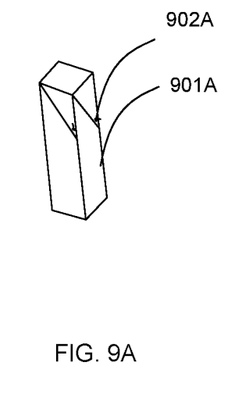
FIG. 9A shows an isometric view of a sixth example of a supply drop assembly with multiple folding wings arrangement as stored for transportation.
Figure 9B:
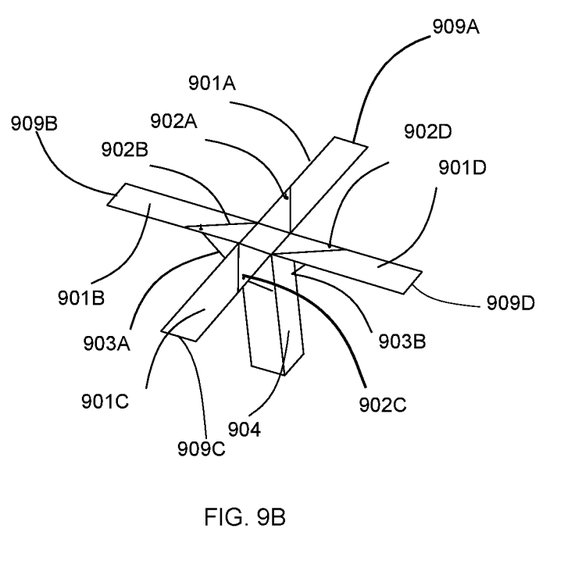
FIG. 9B shows an isometric view of the supply drop assembly of FIG. 9A with the multiple folding wings of FIG. 9A, with wings extended for descent.
Figure 9C:
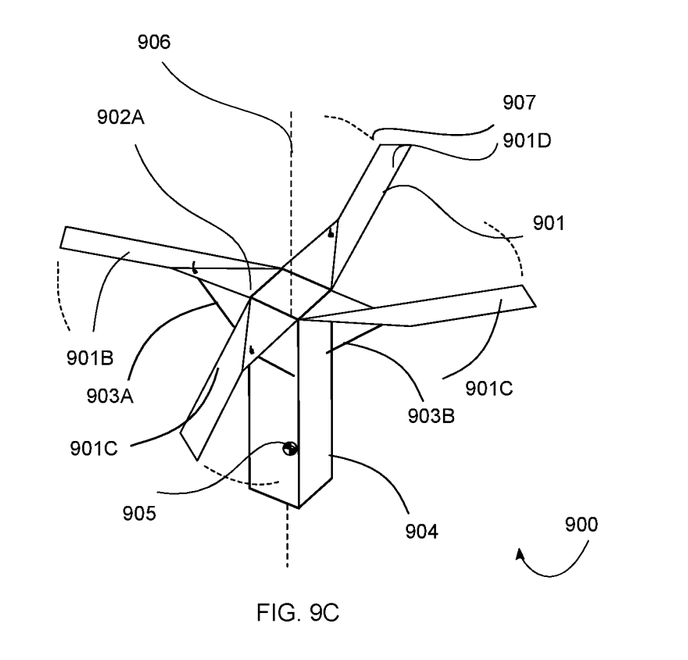
FIG. 9C shows an isometric view of the supply drop assembly of FIG. 9A with the multiple folding wings of FIG. 9A rotating as the assembly descends.

FIG. 9A shows an isometric view of another example of a supply drop assembly 900 with a multiple folding-wing arrangement in a stored position. The assembly with the multi-wing 901A, 901B, 901C, 901D are hinged with hinges 902A, 902B, 902C, 902D. FIG. 9B shows the multi-wings 901A, 901B, 901C, 901D of FIG. 9A as it begins descent. The multi-wings 901A, 901B, 901C, 901D are deployed, but have not yet rotated up along the hinges 902A, 902B, 902C, 902D. Strings 903A, 903B, 903C, 903D prevent the multi-wings 901A, 901B, 902C, 902D from opening too far. A main payload body 904 of the assembly is used to store the payload. FIG. 9C shows the assembly as it begins to descend. The assembly 900 rotates around its center of gravity 905 and the axis of descent 906 as it descends. The wing tips 909A, 909B, 909C, 909D of each of the multi-wings 901A, 901B, 902C, 902D trace a substantially helical path 907 in the air.

In some embodiments, the assembly incorporates a structure or structures called wing vanes which extend up and or down from the wing surface, and act to keep the airflow over the wing moving along the airfoil. These structures increase the drag on the wing but also increase the lift generated by the wing, slowing descent. In some embodiments, such as a folding embodiment like that shown in FIG. 7B, the wing may be configured to extend and maintain a form with peaks and valleys, or ridges, and not go completely flat. In this embodiment, the ridges in the wing act as wing vanes. Another embodiment with features that act as wing vanes is an embodiment with an inflatable wing consisting of tubes along the airfoil direction.

Because the assembly is falling through the air and rotating, some sections of the wing have a large effective angle of attack, which results in flow separation. Flow separation increases drag and decreases the lift generated by the wing. In some embodiments, the leading edge of the wing incorporates a shape or structure designed to help flow reattach to the wing so the wing can generate more lift, improving performance. The shape may be rounded, or it may consist of serrations that help form smaller leading edge vortices.

In some embodiments, the assembly consists of a rigid, flat wing attached rigidly to the package. In such an embodiment, the wing may be constructed with compostable materials so as not to adversely effect the environment. In this embodiment, multiple packages can be packed flat and stacked on each other, increasing the volume of payload that can be dropped in one delivery.

In some embodiments, the wings and payload body are made of cardboard and are integral to each other. The wings fold down for storage, but extend as the package falls through the air. A mechanical limiter prevents the wings from opening too far. The wings cause the package to rotate, generating lift and slowing the fall of the package.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A supply drop assembly for delivering one or more payloads which falls to the ground from an aerial vehicle, comprising:
   one or more payload bodies each configured to receive a payload; and
   a wing attached to each corresponding payload body; wherein each wing has
   a distal end tip, and
   a root tip near the payload body, and the supply drop assembly has a center of gravity, and
   a spanwise axis that extends along a length of each wing between the corresponding center of gravity and the corresponding distal end tip such that the spanwise axis divides the wing into a first side of the wing and a second side of the wing,
   a leading edge is on the first side of the wing, and
   a trailing edge is on the second side of the wing; wherein each wing is planar and has a lobe that extends away from the spanwise axis in the plane of the wing, wherein the lobe is formed on the second side of the wing such that the second side of the wing is larger than the first side of the wing, and is positioned closer to the root tip, and the lobe is adapted to encourage autorotation when the supply drop assembly falls.

2. The supply drop assembly of claim 1, wherein the mass of the supply drop assembly is arranged to encourage autorotation.

3. The supply drop assembly of claim 1, wherein the wing has an inflatable chamber adapted to be inflated as the supply drop assembly falls to the ground.

4. The supply drop assembly of claim 3, further comprising an air inlet and a one-way valve connecting the air inlet to the inflatable chamber, wherein the air inlet is adapted to receive air as the supply drop assembly falls, the air passes through the one-way valve to inflate the inflatable chamber.

5. A supply drop assembly for delivering one or more payloads which falls to the ground from an aerial vehicle, comprising:
   one or more payload bodies each configured to receive a payload; and
   a wing attached to each corresponding payload body; wherein each wing has a distal end tip, and a root tip near the payload body, and the supply drop assembly has a center of gravity, and a spanwise axis extends along a length of each wing between the corresponding center of gravity and the corresponding distal end tip such that the spanwise axis divides the wing into a first side of the wing and a second side of the wing, a leading edge is on the first side of the wing, and a trailing edge is on the second side of the wing;
   wherein each wing comprises an inflatable chamber further comprising an inlet valve configured to receive a gas to expand the chamber; and
   wherein each wing further comprises one or more ribs extending from the payload body.

6. The supply drop assembly of claim 1, wherein the wing has a leading edge having a rounded airfoil profile.

7. The supply drop assembly of claim 1, wherein the supply drop assembly further comprises a beacon for determining a location of the assembly.

8. The supply drop assembly of claim 1, wherein the supply drop assembly is buoyant in water.

9. The supply drop assembly of claim 1, wherein wing contains one or more creases adapted to encourage autorotation of the assembly.

* * * * *